United States Patent [19]

Cahiez et al.

[11] Patent Number: 5,091,598
[45] Date of Patent: Feb. 25, 1992

[54] MANUFACTURE OF TERTIARY AND SECONDARY ALCOHOLS BY THE ACTION OF AN ORGANIC HALOGEN COMPOUND AND MANGANESE ON A COMPOUND CARRYING A CARBONYL GROUP

[75] Inventors: Gérard Cahiez; Pierre-Yves Chavant, both of Paris; Pierre Tozzolino, Morlaas, all of France

[73] Assignee: Societe Nationale Elf Aquitaine, France

[21] Appl. No.: 290,997

[22] Filed: Dec. 28, 1988

[30] Foreign Application Priority Data

Dec. 30, 1987 [FR] France ............... 87 18352

[51] Int. Cl.⁵ ............... C07C 29/14; C07C 29/143; C07C 29/136
[52] U.S. Cl. ............... 568/878; 260/410; 558/451; 560/179; 560/266; 568/813
[58] Field of Search ............... 568/878, 813; 560/266, 560/179; 558/451

[56] References Cited

U.S. PATENT DOCUMENTS

| | | | |
|---|---|---|---|
| 2,414,012 | 1/1947 | Boord | 568/878 X |
| 2,838,576 | 6/1958 | Normant | 568/878 |
| 3,308,172 | 3/1967 | Rudner et al. | 568/878 |
| 3,423,446 | 1/1969 | Kobetz et al. | 568/878 X |

OTHER PUBLICATIONS

"Les Organomanganeux: utilisations en synthese organique" by G. Cahiez, L'Actualite Chimique, Sep. 1984, p. 27.
"Carbon-Carbon Bond Formation with Metallic Manganese" by T. Hiyama et al., Chemistry Letters, pp. 1237-1238, 1983.

Primary Examiner—Joseph Paul Brust
Attorney, Agent, or Firm—Ostrolenk, Faber, Gerb & Soffen

[57] ABSTRACT

Process of preparation of alcohols by the reaction of an organic halide with a carbonyl compound in an organic solvent, in the presence of metallic manganese, followed by hydrolysis of the reaction product; the reaction is initiated and activated by an ester present in the reaction medium.

17 Claims, No Drawings

MANUFACTURE OF TERTIARY AND SECONDARY ALCOHOLS BY THE ACTION OF AN ORGANIC HALOGEN COMPOUND AND MANGANESE ON A COMPOUND CARRYING A CARBONYL GROUP

The present invention relates to an improvement in the preparation of secondary and tertiary alcohols. It relates especially to the preparation of such alcohols by the action of an organo-manganous compound on a compound carrying a carbonyl group.

The utility of secondary and tertiary alcohols is well known in the synthesis of natural products; among standard methods for their preparation, those based on the use of organo-metallic reactants are very interesting because they allow the preparation of various types of tertiary alcohols, especially useful in the pharmaceutical field, as well as those relating to aromas and perfumes. The route using organo-metallic compounds has been the subject of various studies, including amongst others those of Barbier ("C.R. Acad. Sci. Paris", Vol. 128, p. 110, 1899) which describes the preparation of alcohols starting with halides, magnesium and carbonyl compounds. This reaction is a modification of that of Wagner and Saytzeef ("Justus Liebigs Ann. Chem.", Vol. 175, p. 351, 1875) utilising zinc and forming the origin of the remarkable development of organo-magnesium chemistry. The use of zinc has been the subject of important studies; it concerns in particular the reaction of an α-bromoester and a carbonyl compound in the presence of zinc. This reaction is generally called the Reformatsky reaction.

Recent studies describe this same type of reaction starting from various metals such as tin, cerium and Zn/Cu, Zn/Cd and Zn/Pb couples in the Reformatsky reaction.

A very clear advance has been realised in this area by the use of organo-manganous compounds, the advantage of which lies in their selectivity during attack on multi-functional molecules. Thus according to G Cahiez ("L'Actualité Chimique", September 1984, p. 27) the organo-manganous compounds react, like numerous organo-metallic compounds, with aldehydes and ketones to lead to tertiary alcohols, but they do not attack esters. This selectivity is interesting because it is total, even at ambient temperature.

Up to a recent period, organo-manganous derivatives were obtained by metal-metal exchange starting with lithium and magnesium compounds. This method of preparation precludes access to functional organo-manganous compounds such as $X-MnCH_2-CO_2Et$ alone because the lithium or magnesium starting compound cannot be obtained. This shows the advantage of preparing organo-manganous compounds directly from metallic manganese and an organic halide. Recently, Hiyama et coll. ("Organometallics" 1982, 1, 1249-1251) describe the reactivity of manganese metal obtained by reduction with the aid of the hydride $LiAlH_4$ of manganese chloride (II) with respect to allyl bromides; the reactant obtained, treated by an aldehyde or a ketone, leads to the corresponding tertiary alcohol. According to a later publication ("Chemistry Letters", p. 1237-38, 1983), the use of micronised manganese is economically very interesting. However, the attainment of good yields necessitates the use of excessive quantities of the reactants; metal/ketone or aldehyde ratios=7/1, halide/ketone or alcohol=6. Moreover, the reaction requires 1 eq. of iodine for a reflux for a dozen hours. This thus concerns an array of conditions which render the industrial exploitation of such syntheses very hypothetical.

The present invention provides a new solution which allows the production of all kinds of secondary or tertiary alcohols by the action of an organic halide, metallic manganese and an organic compound carrying a carbonyl, at temperatures around the ambient, and under good economic conditions. The invention allows in effect the production of the desired alcohols more rapidly and in better yields than has been possible according to the prior art.

The process according to the invention, which consists in reacting an organic halide with an organic compound carrying at least one carbonyl group within an organic solvent, in the presence of metallic manganese as a powder and then hydrolysing the product formed, is characterised in that the reaction with the manganese is initiated and activated by the presence of an ester.

Thus the reaction is accelerated and its yield augmented by the use of an ester in the organic solution or in suspension in the substances indicated above. The invention can be carried out by the addition of an appropriate ester to the solvent used; when the reactants are soluble in this ester, the preferred form of operation of the invention consists in employing the ester itself as the liquid of the reaction medium.

The improvement in the preparation of alcohols according to the invention is obtained more particularly with the aid of esters of a relatively low molecular weight, particularly those where the total number of carbon atoms is from 3 to 13. In other words, the carboxylic acid of the ester comprises 2 to 12 C and its alcohol residue is from $C_{12}$ to $C_1$ respectively. Thus use can be made of esters of acids such as acetic, propionic, butyric, caproic, benzoic, etc., of methyl, ethyl, propyl, butyl, octyl or others. However, particularly interesting results are obtained with more economical solvents which comprise $C_2$ to $C_4$ aliphatic acids with $C_1$ to $C_3$ alcohols; these include the acetates, propionates, butyrates and iso-butyrates of methyl, ethyl, propyl or isopropyl. Economically, ethyl acetate constitutes a solvent of choice for carrying out the invention.

According to a particular embodiment of the invention, an equal improvement in the production of secondary alcohols is obtained, as also with that of tertiary alcohols; this embodiment consists in the addition to the reaction medium of a compound of a metal less electropositive than manganese, at the same time as an ester. Thus, the reaction is activated by the addition to the medium, in the organic solvent constituted by or containing an ester, of a salt such as a halide, sulphate, acetate or other of a metal of Groups II to VIII of the Periodic Classification of the Elements less electro-positive than Mn.

Particularly suitable are compounds of the metals Zn, Cd, Sn and Hg and especially Zn. The quantity of the metal compound is in general from 1 to 200% equivalents per liter of solution forming the reaction medium and preferably from 2 to 10%.

When the metal compound is present in the reaction medium in conjunction with one or more of the esters described above, the organic compound having the carbonyl group can be an aldehyde and then a secondary alcohol is obtained. The production of tertiary alcohols from ketones occurs with even better yields than when employing an ester alone, without a metal compound.

Standard solvents, known for their use in the prior art relevant to the process of the invention, particularly ethers and if required aliphatic or aromatic hydrocarbons or chlorinated solvents, can be employed, added to the ester according to the invention. In general, they are used in an amount of 5% to 90% by weight and preferably from 50% to 90%. In this way, where the products of the reaction are partially soluble, use can be made for example of THF, diethylether, heptane, octane, benzene, toluene, acetonitrile, DMF, trichloroethane etc., including a compatible proportion of the ester.

As indicated above, it is generally very advantageous to utilise one or more esters themselves as the solvent for the reaction.

The range of reactions which form the process of the invention can be represented in the following manner:

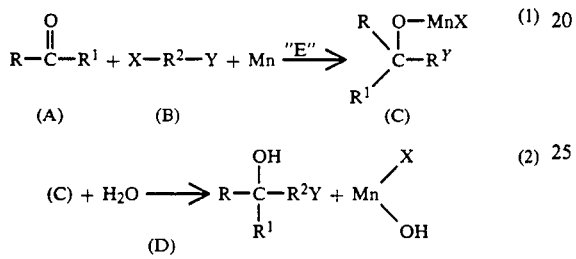

The reaction (1) takes place within a solvent in which preferably the two reactants (A) and (B) are soluble. The principle of the invention resides in the addition of an activating ester "E".

The organo-manganous compound (C) can be separated from the reaction medium in order to undergo hydrolysis (2); in particular the solvent can be evaporated after the reaction (1) and the residue treated with water in a manner known per se. Hydrolysis can also take place directly in the solvent after the reaction (1). It is generally effected in acid medium and the Mn is recovered in the form of its salt $MnX_2$.

The compound (A) is an aldehyde when $R^1$ is H or a ketone when R and $R^1$ are hydrocarbon groups; these can be aliphatic, preferably from $C_1$ to $C_8$, cycloaliphatic, especially from $C_4$ to $C_8$, and/or aryl, particularly phenyls or napththyls which can carry alkyl, alkenyl, halogen or other substituents.

R in the case of an aldehyde and R and/or R1 in the case of a ketone can carry functions such as ester, nitrile, ether, sulphide, halide, acetal.

Thus the reactant (A) can be for example such as acetaldehyde, propionaldehyde, butyraldehyde, phenylacetaldehyde, benzaldehyde, cinnamic aldehyde, anisaldehyde, etc.

It can be constituted by a ketone of the acetone type, dipropylketone, methylethylketone, methylheptenone, cyclopentanone, methylcyclohexanone, methyl acetylpropionate, acetophenone, benzophenone, menthone, naphthylmethylketone, etc.

In the organic halide (B), the letter X designates a halogen, especially Br. $R^2$ designates a hydrocarbon group. Y, the presence of which is not obligatory, represents a functional group, such as for example —COOH nitrile, amide or a group with a double or triple bond. The organic halide can be allyl, propargyl, benzyl or an α-halogen-ester or nitrile. Thus the compound $X-R^2-Y$ can be for example, $Br-CH_2-CH=CH_2$; $Cl-CH_2-CH=CH_2$; $Br-CH_2C_6H_5$; $Br-CH_2-C(CH_3)=CH_2$; $Br-CH_2-CO_2Et$; $I-CH_2-CH=C(CH_3)_2$.

The substances cited above only constitute non-limitative examples of the compounds (A) and (B) and are given only as a guide.

The process according to the invention can be carried out with stoichiometric ratios of the reactants (A), (B) and Mn in the reaction (1). However, it has proved preferable to operate with a certain excess of the metal Mn and of the compound (B) with respect to the carbonyl compound (A). In effect, the yields of secondary or tertiary alcohol are increased when Mn and (B) are in excess with respect to stoichiometry. In a general manner, it is useful to employ 1 to 3 atoms of Mn and 1 to 2 moles of (B) per mole of the carbonyl compound (A). The preferred proportions range between 1.2 and 1.6 atoms of Mn and 1.1 and 1.5 moles of the halide (B).

On the other hand, it is advantageous to work with solutions which are sufficiently but not too concentrated in the compound (A), particularly 0.3 to 2M solutions and preferably 0.5 to 1.6M.

The temperature during stage (1) of the process can range between 20° C. and 100° C., the range from 30° C. to 60° C. being preferable.

The particle size range of the manganese employed is from 1 to 2000 microns and preferably from 10 to 500 microns. It is also possible, for reactions on a larger scale, to utilise average particle sizes greater than 2000 microns.

Addition of the reactants should be effected during a period which in general is of the order of 1 to 6 hours and most frequently is from 3½ to 4½ hours; this constitutes a marked advantage over the prior art which requires 12 hours or more of reaction time. Owing to the addition of the activator ester, the reaction starts after 30 to 40 minutes, while it only commences after about 2 hours in the known process using manganese powder.

With respect to the process described above, the addition of salts of Zn, Cd, Hg, Sn, etc., soluble at least partially in the reaction medium and particularly the halides, in an amount of 1 to 200% with respect to the carbonyl compound and preferably 2 to 10% allows a considerable improvement in certain yields. This is so for halides, in the case of allyl chloride and the α-chloroesters and when the carbonyl compound (A) is an aldehyde RCHO or a methylated ketone $RCOCH_3$, R being defined as before.

The invention is illustrated by the non-limitative examples given below in which the following mode of operation is employed.

The reactor comprises a 3-necked flask of 100 ml capacity, provided with a mechanical agitator, mounted so as to cause movement of the Mn powder which is placed in the reactor. This also comprises a thermometer and a nitrogen input tube allowing an inert atmosphere to be established in the apparatus, throughout the operations. The reactor is placed in a water bath maintained at the desired temperature.

The manganese is 98-99% coarse powder having a particle size ranging between 10 and 500 microns. It is charged to the flask with the metal activator salt and covered with the solvent. The reaction is initiated by several drops of the organic halide (B), $XR^2Y$ as soon as the metal has undergone a change of colour and when heating has been produced, progressive introduction of the reactants (A) and (B) is begun with the aid of pumps. At the end of this introduction, which lasts several hours, agitation of the medium is continued for 15 to 30 mn at the same temperature which has been used for reaction (1). Then the reaction medium is mixed with approximately its own volume of water at 20° C., slightly acidified with HCl in order to modify the pH of the water to 7 or to a slightly lower value, in order to dissolve the metallic salts present. The desired product is extracted with ether and washed with Na bicarbonate. The yield of the alcohol obtained with respect to the compound (A) is calculated from the quantity of alcohol isolated by extraction and distillation. EXAMPLES 1 TO 3

Preparation of 4-allyl-heptanol-4 comparatively according to the prior art and according to the invention Operating as indicated above, 1 mole of dipropylketone $CH_3CH_2CH_2-CO-CH_2CH_2-CH_3$ is reacted with 1.1 mole of allyl bromide $CH_2=CH=CH_2Br$ and 1.3 atoms of metal powder Mn in well-dried tetrahydrofuran in the proportion of 0.7 liter of this solvent for the quantities indicated. The reaction takes place at 60° C. for 4 hours.

EXAMPLE 1

Nothing else is added to the reaction medium. The reaction cannot be initiated. It starts during addition of the reactants and leads after about 4 hours to a yield of tertiary alcohol of only about 16%.

EXAMPLE 2

In the reaction medium described above, 50% of the THF is replaced by dry ethyl acetate. The reaction starts several minutes after introduction of the reactants. The yield after 4 hours at 50° in tertiary alcohol is 58% with respect to the dipropylketone. Activation by ethyl acetate is thus very clear.

EXAMPLE 3

In the reaction medium of the foregoing tests, the solvent THF is replaced completely by the same volume of dry ethyl acetate. It is then found after 4 hours at 50° C. that there is a yield of tertiary alcohol of 73%. The effect of the ester is thus remarkable, in comparison with Example 1.

EXAMPLE 4

Role of the temperature

Example 3 is repeated at four different temperatures for the first stage of the preparation, the concentration of dipropylketone being 1.33M in ethyl acetate. The yields of ketone determined by chromatography are:

| | |
|---|---|
| for 20° C. . . . | 54% |
| for 40° C. . . . | 61% |
| for 50° C. . . . | 73% |
| for 60° C. . . . | 67% |

EXAMPLE 5

Influence of the proportions of the reactants

Identical preparations to those of Example 3 are carried out with variable proportion of the bromide (B) and of Mn. They have led to the following yields, indicated by vapour phase chromatography.

| Moles $CH_2=CH-CH_2Br$ per mole of ketone | Atoms Mn per mole of ketone | Yield % |
|---|---|---|
| 1.0 | 1.5 | 72 |
| 1.0 | 2.5 | 72 |
| 1.5 | 1.5 | 92 |
| 1.5 | 2.5 | 98 |
| 1.8 | 1.5 | 94 |
| 2.0 | 2.5 | 100 |

The excess of the reactants allows very high yields to be attained.

EXAMPLE 6

Effect of the concentration of the ketone

By repeating Example 3 with variable molar concentrations of dipropylketone, with 1.3 mole of the halide and 1.5 atom of Mn, the following yields have been found.

| Concentration of ketone in the reaction medium | Yield % |
|---|---|
| 0.83 M | 83 |
| 1.67 | 92 |

There is thus a certain optimum.

EXAMPLES 7 TO 23

Preparation of various tertiary alcohols starting from various ketones $R-CO-R^1$ with 1.4 mole of alkenyl bromide $CH_2=CH-CH_2Br$ and 1.5 atom of Mn at 50° C. for 4 hours. The yields with respect to the ketone are given in the Table I on the following page.

TABLE I

| No | $R-CO-R^1$ | Yield % |
|---|---|---|
| 7 | $CH_3CH_2CH_2-CO-CH_2CH_2CH_3$ | 85 |
| 8 | $CH_3(CH_2)_3-CO-(CH_2)_3CH_3$ | 86 |
| 9 | $CH_3(CH_2)_4-CO-(CH_2)_4CH_3$ | 74 |
| 10 | $CH_3(CH_2)_6-CO-(CH_2)_6CH_3$ | 81 |
| 11 | $C_6H_5-CO-CH_2CH_2CH_3$ | 91 |
| 12 | $p.Cl-C_6H_4-CO-CH_2CH_3$ | 91 |
| 13 | $C_6H_5-CO-CH_3$ | 78 |
| 14 | $p.CH_3-C_6H_4-CO-CH_3$ | 72 |
| 15 | $p.Br-C_6H_4-CO-CH_3$ | 85 |

TABLE I-continued

| No | R—CO—R$^1$ | Yield % |
|---|---|---|
| 16 | (CH$_3$)$_2$CH—CO—CH(CH$_3$)$_2$ | 68 |
| 17 | (CH$_3$)$_3$C—CO—CH$_2$—CH$_2$—CH$_2$—CH$_3$ (with CH$_3$ on the C) | 62 |
| 18 | (CH$_3$)$_2$C=CH—CO—(CH$_2$)$_3$CH$_3$ | 75 |
| 19 | (CH$_3$)$_2$C=CH—CO—CH$_3$ | 59 |
| 20 | C$_6$H$_{10}$CO (cyclohexanone) | 56 |
| 21 | CH$_3$(CH$_2$)$_3$—CO—(CH$_2$)$_6$COOC$_2$H$_5$ | 87 |
| 22 | C$_2$H$_5$—CO—(CH$_2$)$_{10}$—O—CO—CH$_3$ | 74 |
| 23 | C$_2$H$_5$—CO—(CH$_2$)$_5$Cl | 79 |

According to the operative mode described above prior to the Examples, but adding 0.1 mole of zinc chloride per mole of carbonyl compound, before the stage of initiation of the reaction, good yields are obtained, utilising as the carbonyl derivative an aldehyde. The yields obtained in the case of methylated ketones are also improved.

EXAMPLE 24

Using the operative conditions described above, without addition of the zinc salt, but utilising 1 mole of heptanal, 1.1 moles of allyl bromide, 1.3 gm-atom of manganese and 0.7 liter of ethyl acetate, after 4 hours a yield of 5% of alcohol II is obtained, recovered in the form of the acetate.

EXAMPLE 25

The same test as in Example 24, with 0.1 mole of zinc chloride, provided after 4 hours, leads to a yield of 85% of alcohol II, recovered in the form of the acetate. The effect of the zinc chloride is thus remarkable.

EXAMPLE 26

Operation according to the same procedure as for Example 25, in the presence of 0.05 mole of zinc chloride, starting with 1 mole of heptylmethylketone, 1.3 gm-atom of manganese, 1.1 mole of crotyl bromide and 0.7 liter of ethyl acetate. The yield of tertiary alcohol is 80% with respect to the ketone.

EXAMPLE 27

In the conditions of Example 25, utilising 0.1 mole of zinc chloride, 1.1 mole of ethyl bromoacetate, 1 mole of heptanal, 1.3 gm-atom of manganese and 0.7 liter of ethyl acetate, a 60% yield in the hydroxyester with respect to the heptanal was obtained.

EXAMPLES 28 TO 31

Preparation of various secondary alcohols in the form of the acetate starting from 1 mole of the aldehyde, 1.1 to 1.4 moles of allyl halide, 1.3 gm-atom of manganese and 0.1 mole of zinc chloride at 50°-60° C. for 4 hours. The yields are indicated in Table II:

TABLE II

| Ex No | Aldehyde | Halide (ratio) | Yield % |
|---|---|---|---|
| 28 | (CH$_3$)$_3$C—CHO | BrCH$_2$CH=CH$_2$ (1,1) | 87 |
| 29 | C$_6$H$_5$CHO | BrCH$_2$CH=CH$_2$ (1,4) | 90 |
| 30 | CH$_3$(CH$_2$)$_5$CHO | BrCH$_2$C(CH$_3$)=CH$_2$ (1,1) | 83 |
| 31 | CH$_3$(CH$_2$)$_5$CHO | BrCH$_2$CH=C(CH$_3$)$_2$ (1,1) | 79 |

EXAMPLES 32 TO 38

The operations of Example 27 are repeated with various organic halides and various esters employed as solvents. 1.4 moles of the halide and 1.5 gm-atom of manganese are employed each time, per 1 mole of heptanal. Operation always takes place in the presence of 1.1 mole of acetic anhydride. The yields obtained as the acetate of the secondary alcohol formed are summarised in Table III:

TABLE III

| Ex No | Halide | Solvent | Yield |
|---|---|---|---|
| 32 | ClCH$_2$CO$_2$Et | AcOEt | 50% |
| 33 | BrCH$_2$CO$_2$Et | AcOEt | 86% |
| 34 | C$_6$H$_{13}$CHBrCO$_2$Et | AcOEt | 92% |
| 35 | " | C$_7$H$_{15}$CO$_2$Et | 78% |
| 36 | (CH$_3$)$_2$CHBrCO$_2$Et | AcOEt | 87% |
| 37 | " | Pivalate Et | 71% |
| 38 | C$_6$H$_5$CH$_2$Br | AcOEt | 41% |

We claim:

1. In a process of preparing a secondary or tertiary alcohol by reacting an aldehyde or ketone of the formula RCOR$^1$ where R is an aliphatic hydrocarbon group or a cycloaliphatic group or aryl group optionally substituted by alkyl, alkenyl, ester, amide, nitrile or halide groups and R$^1$ is hydrogen or selected from the same groups constituting R, with an organic halide XR$^2$Y where X is halogen, R$^2$ is a hydrocarbon group and Y represents an optional carboxylate, nitrile or amide group in an organic solvent and in the presence of powdered metallic manganese, hydrolyzing the product obtained as a result of the reaction and separating the secondary or tertiary alcohol thus produced, the improvement which comprises conducting the reaction of the aldehyde or ketone with the organic halide in the presence in the reaction medium of an activator which is an alkyl ester of a carboxylic acid having a total of 3 to 13 carbon atoms.

2. Process according to claim 1, characterized in that the total number of carbon atoms in the ester is from 3 to 13, the carboxylic residue of this ester being from C$_2$ to C$_{12}$ and the alcohol residue being from C$_{12}$ to C$_1$ respectively.

3. Process according to claim 2, characterized in that the ester is derived from a C$_2$ and C$_4$ aliphatic acid and a C$_1$ to C$_3$ alcohol.

4. Process according to claim 1, characterized in that the ester is a propionate, butyrate or iso-butyrate of methyl, ethyl, propyl or isopropyl.

5. Process according to claim 1, characterized in that the ester is ethyl acetate.

6. Process according to claim 1, characterized in that the solvent is utilized in an amount of 5% to 90% by weight of the ester.

7. Process according to claim 1, characterized in that the solvent is constituted entirely by the ester.

8. Process according to claim 1, characterized in that 1 mole of the ketone is reacted with 1 to 2 moles of the organic halide and 1 to 3 gm-atom of manganese, and the concentration of the ketone in the reaction medium is from 0.3 to 2M.

9. Process according to claim 1, characterized in that the reaction medium contains a compound of zinc, cadmium, tin or mercury.

10. Process according to claim 9, characterized in that the metal compound is a chloride, bromide or iodide salt of zinc, cadmium, tin or mercury dissolved at least partially in the reaction medium.

11. Process according to claim 10, characterized in that 1 mole of the aldehyde or ketone is reacted with 1 to 2 moles of the organic halide, 1 to 3 gm-atom of manganese and 0.01 to 1 mole of the metal salt, the concentration of the carbonyl compound in the reaction medium being from 0.3 to 2M.

12. Process according to claim 9, characterized in that the reaction between the aldehyde or ketone, the organic halide and the manganese takes place between 20° and 100° C..

13. Process according to claim 6, characterized in that the solvent in utilized in amount of 50-90% by weight of the ester.

14. Process according to claim 8, characterized in that the ketone concentration is from 0.5 to 1.6M.

15. Process according to claim 10, characterized in that the salt is a zinc halide.

16. Process according to claim 11, characterized in that the amount of metal salt is 0.05-0.1 mole, the concentration of the aldehyde or ketone is 0.5-1.6M.

17. Process according to claim 12, characterized in that the reaction temperature is between 30° and 60° C.

* * * * *